United States Patent [19]

Hansen

[11] 4,195,524

[45] Apr. 1, 1980

[54] METHOD AND APPARATUS FOR COLLECTING AND STORING ENVIRONMENTAL GASES

[75] Inventor: Robert G. Hansen, Santa Barbara, Calif.

[73] Assignee: Air Products and Chemicals, Inc., Allentown, Pa.

[21] Appl. No.: 956,312

[22] Filed: Oct. 31, 1978

[51] Int. Cl.² ............................................. G01N 1/24
[52] U.S. Cl. ............................................. 73/421.5 R
[58] Field of Search ................................. 73/421.5 R

[56] References Cited

FOREIGN PATENT DOCUMENTS 1113875 5/1968 United Kingdom ............... 73/421.5 R

*Primary Examiner*—S. Clement Swisher
*Attorney, Agent, or Firm*—James C. Simmons; E. Eugene Innis

[57] ABSTRACT

A method and apparatus to collect and store a sample of an environmental gas, e.g. air. A sample container or bottle is cooled below the condensation temperature of the environmental gas so that a partial vacuum is created in the container thus permitting environmental gas to be drawn into the bottle and condensed. Included in the apparatus are means to meter the quantity of environmental gas admitted to the bottle.

11 Claims, 1 Drawing Figure

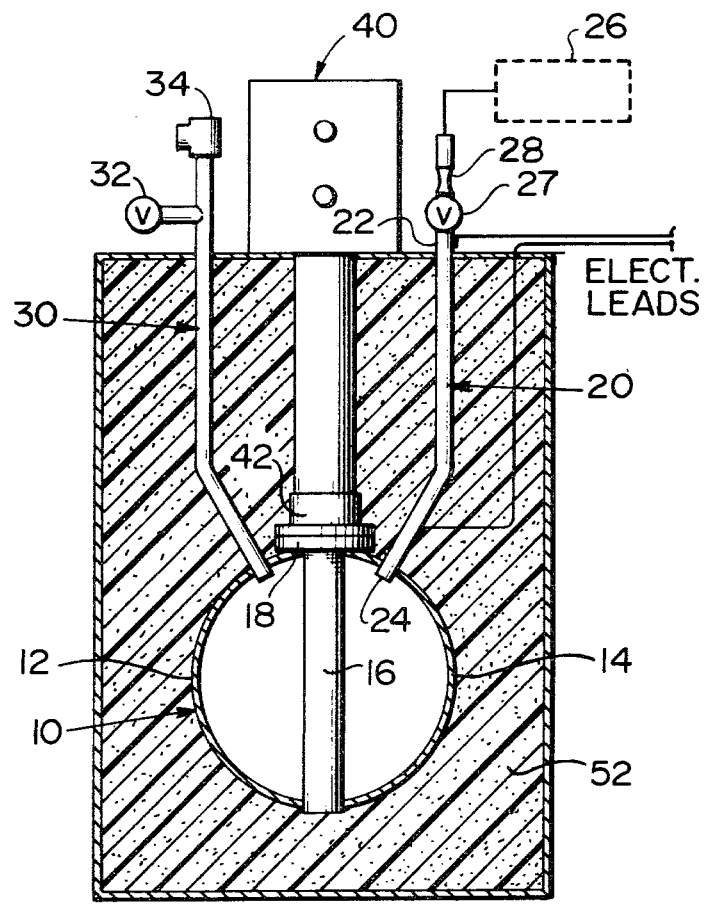

METHOD AND APPARATUS FOR COLLECTING AND STORING ENVIRONMENTAL GASES

BACKGROUND OF THE INVENTION

1. Field of the Invention

This invention pertains to a method and apparatus for collecting and storing a sample of an environmental gas such as air. Over the past several decades, man has become more conscious of his environment and, particularly, the air he breathes. With the advent of the industrial revolution, new sources of air pollution occur causing harmful materials to be discharged into the atmosphere so that it has become more and more important to monitor the earth's atmosphere. This is particularly true in areas where nuclear explosive devices have been tested, nuclear power plants operate and other highly concentrated industrial environments. One method of sampling the environment is to accumulate a sample of the air and condense it to where it becomes liquid and subsequently vaporize the liquid sample and pass it through a gas analyzer to test it for various components.

2. Description of the Prior Art

The most common method of sampling an environmental gas such as air has been to utilize a conventional compressor to force the air under pressure into a sample container. One of the problems associated with this method is the possibility of contaminating the sample due to the use of oils and other lubricants in the air compressor. Air samples have been gathered by utilizing a liquefied gas to condense the air inside a precooled container. The air sample is then taken to a laboratory where the container is allowed to warm to ambient temperature thus revaporizing the liquid to the gaseous state, and the gaseous sample then is passed through the required analyzer.

SUMMARY OF THE INVENTION

The present invention overcomes the prior art problems and provides a method of collecting a contamination-free sample by utilizing a cryogenic refrigerator to condense and store the sample to be subsequently analyzed. If the apparatus is to be utilized to sample air, the sample container is cooled to below 78.8° K. to create a partial vacuum inside the container and maintain the gathered sample in liquid form.

Therefore, it is the primary object of the present invention to provide a method and apparatus for collecting and storing a sample of an environmental gas.

It is a further object of the present invention to provide a method and apparatus for sampling air.

It is still another object of the present invention to provide a method and apparatus utilizing a cryogenic refrigerator to collect an air sample by condensation of the air.

It is yet another object of the present invention to provide a method and apparatus for collecting and storing noncontaminated environmental gas samples.

BRIEF DESCRIPTION OF THE DRAWING

The single FIGURE of the drawing is a schematic representation of one embodiment of the present invention.

DETAILED DESCRIPTION OF THE PREFERRED EMBODIMENT

Referring to the drawing, the numeral 10 indicates a sample container or bottle in the form of a sphere. The bottle 10 can be fabricated in two hemispherical portions 12 and 14 supported around a heat conducting support (post) 16. The post 16 is preferably fabricated from a good heat conductor such as copper, and has on one end thereof an adapter 18 for mating with a refrigerator as will be hereinafter more fully described. In the embodiment of the invention shown, there is a first or inlet conduit 20 having a first end 22 which serves as an inlet, and a second end 24 which terminates in an opening disposed within the sample collector or bottle 10. The conduit 20 can be fixed to the bottle 10 as by welding or brazing as is well-known in the art. At the inlet end of conduit 20, there is a shut-off valve 27 and a metering orifice (valve) 28, the purpose of which will be hereinafter more fully described. Also associated with the inlet is an optional drier 26 for predrying the incoming air. Outlet conduit 30 serves as a means for withdrawing collected sample and as a vent. Conduit 30 is typically identical to conduit 20, and affixed to the bottle 10 in an identical manner. At the outlet end of conduit 30, there is a sample withdrawing valve 32 and a pressure relief valve 34.

In order to cool the sample collector 10, a cryogenic refrigerator 40, such as Model DE102 supplied by Air Products and Chemicals, Inc., Allentown, Pa., is utilized. Refrigerator 40 is a single stage displacer-expander type refrigerator operated by a remote compressor and has a cold end having thereon a cold shoe 42 which mates with adaptor 18 of heat conducting and support post 16 to provide good thermal contact with the sample container 10.

As shown in the drawing, the major portions of the sample bottle 10, inlet conduit 20, outlet conduit 30, and the cold finger of the cryogenic refrigerator 40 can be placed within a support housing 50 filled with a suitable insulation such as synthetic foam 52.

The sample bottle 10 and conduits 20 and 30 are preferably fabricated from a structural material such as stainless steel and can be made to be lightweight.

In order to achieve the lightweight structure, the cryogenic refrigerator disclosed is preferable, however, it is not necessary that the cryogenic refrigerator be of the type utilizing a remote compressor. To do so only minimizes the weight of the overall system.

The metering orifice 28 is installed in the inlet line to set the rate at which the sample is drawn into the bottle 10.

Thus, the system shown in the drawing consists of a cryogenic refrigerator having a cold end (expander) separate from the compressor which can produce refrigeration at a temperature below 75° Kelvin (°K.). The gas sample bottle 10 is sized to contain a specific quantity of the gas being sampled in liquid form. The system includes an inlet tube, preferably of stainless steel with a gas metering orifice 28 at the inlet, and a separate stainless steel vent tube 30 with a pressure relief valve 34.

After the apparatus is assembled, according to the drawing and the foregoing description, it can be operated as follows. First, the sample bottle 10 is evacuated and, if necessary, heated to approximately 150° F. to drive out contaminants. Depending upon the nature of insulation 52, it may have to be removed during the period when the bottle is heated. If this is the case, after bottle 10 is cooled to ambient temperature, the insulation is replaced around the bottle. The refrigerator 40 is then activated, and the system is allowed to cool down.

As the system is cooled to below 75° K., the inlet shut-off valve 27 is opened causing a sample of the environment (e.g. air) to be drawn into the sample container 10 since it is partially evacuated. Sample holder 10, being at a temperature below 75° K., will cause the air sample to condense and thus be stored within container 10. At the time the sample is to be analyzed, the system can be allowed to come to ambient temperature by turning off the refrigerator 40 withdrawing the sample through valve 32 and putting the sample through an analyzer.

As set out above, the system operates on the principal that below 78.8° K. air, if this is the gas being sampled, liquefies. The sample holder 10, cooled to this temperature, creates a partial vacuum in the bottle which permits the sample of ambient air to be drawn into the bottle and condense. The sample so collected is not contaminated since the bottle is clean to start with, and the sample has not passed through a compression device. As is well-known, as long as the pressure in the sample bottle 10 is less than the critical pressure for the orifice, the flow rate of gas through the orifice into the bottle will be constant. The equation for the critical pressure is $$\frac{Pc}{P} = \left(\frac{2}{k+1}\right)\frac{k}{k-1}$$

Pc—Critical pressure downstream of orifice
P—Ambient pressure at inlet to orifice
k—Ratio of specific heats for the gas Air has a value of k=1.4; therefore, the pressure in the sample bottle must be less than 53% of the ambient air pressure for the flow rate to be constant. For sea level conditions, the temperature of the liquid in the sample bottle must be less than about 73° K. for the vapor pressure to be less than 0.53 atmospheres absolute.

It is also desirable to limit the minimum bottle temperature so that the sample does not freeze. This is done to avoid the possibility of rupturing the bottle when the sample melts after having frozen. For air, a minimum temperature of about 65° K. is required to avoid freezing the sample. Control of temperature between 65° K. and 73° K. may be accomplished by adjusting the amount of insulation to have the heat losses match the refrigeration rate. It may more preferably be done by using an electric heater in combination with a temperature sensor/controller as is well-known in the art.

In use, as bottle 10 becomes full with liquid, and liquid begins to fill the inlet tube 20, the surface of the liquid in inlet tube 20 would heat to a temperature of at least 78.8° K., thus equalizing the pressure in the inlet tube and thus no further sampling would be taken since the pressure in the inlet tube would be the same as across the metering orifice 20.

The invention, according to the previous description of the drawing, includes the following features which are believed to be unique and not heretofore known.

(a) A metering orifice 28 installed in the inlet line to set the rate at which a sample is drawn, assuming the bottle pressure is less than 0.5 atmospheres at approximately 73° K.

(b) Foam insulation 52 used to minimize weight and cost.

(c) The entire system or unit can operate unattended in any location where electrical power is available.

(d) The inlet and vent tubes are made of stainless steel to minimize heat leak. Electrical leads can be fastened to the tubes or passed through the tubes to provide heating to eliminate any blockage due to freezing of the gas being sampled.

(e) The sample is not contaminated since it does not pass through a compressor or other apparatus which could be the source of contamination.

(f) The sample bottle is lightweight and designed for a pressure from vacuum to 15 psig. Utilization of a center support post with the bottle also aids in heat transfer from the refrigerator to the sample container.

(g) Unattended operation of the apparatus permits sampling in hazardous environments.

In view of the foregoing features, the system can be designed to be lightweight and portable with rapid cooldown, e.g. on the order of 30 minutes. It is possible when the refrigerator is turned off and the sample warms to have it boil off and flow directly into a gas analyzer without the need for intermediate containment and thus avoid further opportunities for contamination. A separate withdrawal/vent line provides an added safety feature. The internal reinforcing post 16 provides a condensing surface for the sample and helps maintain a uniform temperature and provides internal structural support for the sample container 10. Lastly, the inclusion of electrical leads can provide a mechanism for removing blockages in the event of a freeze-up in the system.

As stated above, when utilizing the apparatus of the present invention to sample air, as long as the sample container is maintained at a temperature of between 65° K. and 78.8° K., the collected sample will remain liquefied. Until the sample container 10 is filled, there will be a partial vacuum within the sample container 10 thus continuing the collection process and the metering orifice 28 will continue to admit a sample in accordance with the orifice setting.

The invention can be applied to sampling other gaseous atmospheres as long as the refrigerator is set to operate at temperature ranges that will maintain the sample in liquid form inside the container 10.

Having thus described my invention, what is desired to be secured by Letters Patent of the United States is set out in the appended claims.

I claim:

1. A method of collecting and storing a sample of an environmental gas, e.g. air, comprising the steps of:
   providing a sample bottle having a metering orifice for admitting the environmental gases;
   cooling said sample bottle below the temperature at which said environmental gas condenses to create a partial vacuum in said sample bottle thus drawing said environmental gas into said bottle;
   maintaining said temperature of said bottle to prevent evaporation or freezing of said collected sample; and
   continuing collection of said sample at a constant rate until the desired sample is obtained.

2. A method according to claim 1 wherein said gas is air.

3. A method according to claim 2 wherein said bottle is cooled to and maintained at a temperature of less than 73 degrees Kelvin and above 65 degrees Kelvin.

4. A method according to claim 1 wherein said bottle is maintained at a temperature less than the saturation temperature corresponding to the critical pressure, but greater than the freezing temperature of the gas being sampled.

5. A method according to claim 1 wherein said collection continues until said bottle is full.

6. An apparatus for collecting and storing a sample of environmental gas comprising in combination:
- a sample bottle or container having means for admitting and discharging a quantity of environmental gas;
- means to meter the quantity of environmental gas admitted to said sample bottle; and
- means to cool said sample bottle below the temperature at which said environmental gas condenses; whereby when said sample bottle is cooled below said condensation temperature a partial vacuum is created in said bottle thus permitting environmental gas to be drawn into said bottle and condensed.

7. An apparatus according to claim 6 wherein said sample bottle is constructed from a lightweight structural metal.

8. An apparatus according to claim 6 including separate inlet and outlet conduits, said inlet conduit including a gas metering orifice at its inlet end.

9. An apparatus according to claim 6 wherein said means to cool said sample bottle includes a cryogenic refrigerator removably connected to said sample bottle.

10. An apparatus according to claim 6 wherein said sample bottle and a portion of said cooling means are surrounded by insulating means.

11. An apparatus according to claim 10 wherein said insulation is a lightweight synthetic foam.

* * * * *